(12) United States Patent
Quinn

(10) Patent No.: US 7,988,658 B2
(45) Date of Patent: Aug. 2, 2011

(54) CATHETER AND METHOD OF MANUFACTURE

(75) Inventor: David G. Quinn, Grayslake, IL (US)

(73) Assignee: Radius International Limited Partnership, Grayslake, IL (US)

( * ) Notice: Subject to any disclaimer, the term of this patent is extended or adjusted under 35 U.S.C. 154(b) by 1543 days.

(21) Appl. No.: 11/108,402

(22) Filed: Apr. 18, 2005

(65) Prior Publication Data

US 2005/0182354 A1    Aug. 18, 2005

Related U.S. Application Data

(63) Continuation of application No. PCT/US2004/037101, filed on Nov. 5, 2004.

(60) Provisional application No. 60/517,826, filed on Nov. 6, 2003.

(51) Int. Cl.
*A61M 3/00* (2006.01)

(52) U.S. Cl. .................. 604/43; 604/6.16; 604/266

(58) Field of Classification Search .......... 604/43, 604/6.16, 19, 27, 264, 266, 270, 523
See application file for complete search history.

(56) References Cited

U.S. PATENT DOCUMENTS

| | | |
|---|---|---|
| 1,696,018 A | 12/1928 | Schellberg |
| 1,879,249 A | 9/1932 | Honsaker |
| 2,116,083 A | 5/1938 | Rüsch |
| 3,384,089 A | 5/1968 | Shriner |
| 3,589,368 A | 6/1971 | Jackson et al. |
| 3,812,860 A | 5/1974 | Gilbert et al. |
| 3,881,254 A | 5/1975 | Epstein |
| 4,037,599 A | 7/1977 | Raulerson |
| 4,134,402 A | 1/1979 | Mahurkar |
| 4,270,542 A | 6/1981 | Plumley |
| 4,311,140 A | 1/1982 | Bridgman |
| 4,368,737 A | 1/1983 | Ash |
| 4,381,011 A | 4/1983 | Somers, III |
| 4,388,076 A | 6/1983 | Waters |
| 4,390,017 A | 6/1983 | Harrison et al. |
| 4,410,320 A | 10/1983 | Dykstra et al. |
| D272,651 S | 2/1984 | Mahurkar |
| 4,445,897 A | 5/1984 | Ekbladh et al. |
| 4,490,143 A | 12/1984 | Quinn et al. |
| 4,496,347 A | 1/1985 | MacLean et al. |
| 4,498,902 A | 2/1985 | Ash et al. |
| 4,516,970 A | 5/1985 | Kaufman et al. |
| 4,529,399 A | 7/1985 | Groshong et al. |
| 4,549,879 A | 10/1985 | Groshong et al. |
| 4,552,554 A | 11/1985 | Gould et al. |
| 4,559,039 A | 12/1985 | Ash et al. |

(Continued)

FOREIGN PATENT DOCUMENTS

CA    1 150 122    7/1983

(Continued)

*Primary Examiner* — Nicholas D Lucchesi
*Assistant Examiner* — Quynh-Nhu H Vu
(74) *Attorney, Agent, or Firm* — Brinks Hofer Gilson & Lione

(57) ABSTRACT

A blood vessel catheter includes a dual lumen catheter tube and a bolus insert attached to the distal end of the tube. First and second ports are formed between the nose section of the bolus and distal end openings of first and second lumens in the tube. The catheter is fabricated by insert molding a thermoplastic bolus onto the distal end of a thermoplastic tube.

13 Claims, 7 Drawing Sheets

U.S. PATENT DOCUMENTS

| | | |
|---|---|---|
| 4,568,329 A | 2/1986 | Mahurkar |
| 4,583,968 A | 4/1986 | Mahurkar |
| 4,594,074 A | 6/1986 | Andersen et al. |
| 4,623,327 A | 11/1986 | Mahurkar |
| 4,626,240 A | 12/1986 | Edelman et al. |
| 4,639,252 A | 1/1987 | Kelly et al. |
| 4,671,796 A | 6/1987 | Groshong et al. |
| 4,692,141 A | 9/1987 | Mahurkar |
| 4,692,153 A | 9/1987 | Berlin et al. |
| 4,701,166 A | 10/1987 | Groshong et al. |
| 4,770,652 A | 9/1988 | Mahurkar |
| 4,772,266 A | 9/1988 | Groshong |
| 4,781,678 A | 11/1988 | de Couët |
| 4,808,155 A | 2/1989 | Mahurkar |
| 4,842,582 A | 6/1989 | Mahurkar |
| 4,895,561 A | 1/1990 | Mahurkar |
| 4,898,669 A | 2/1990 | Tesio |
| 4,986,807 A | 1/1991 | Farr |
| 4,995,865 A | 2/1991 | Gahara et al. |
| 5,053,004 A | 10/1991 | Markel et al. |
| 5,167,623 A | 12/1992 | Cianci et al. |
| 5,171,216 A | 12/1992 | Dasse et al. |
| 5,197,951 A | 3/1993 | Mahurkar |
| 5,221,255 A | 6/1993 | Mahurkar et al. |
| 5,221,256 A | 6/1993 | Mahurkar |
| 5,242,398 A | 9/1993 | Knoll et al. |
| 5,322,519 A | 6/1994 | Ash |
| 5,336,177 A | 8/1994 | Marcus |
| 5,348,536 A | 9/1994 | Young et al. |
| 5,374,245 A | 12/1994 | Mahurkar |
| 5,378,230 A | 1/1995 | Mahurkar |
| 5,395,316 A | 3/1995 | Martin |
| 5,451,206 A | 9/1995 | Young |
| 5,451,216 A | 9/1995 | Quinn |
| 5,451,233 A | 9/1995 | Yock |
| 5,472,417 A | 12/1995 | Martin et al. |
| 5,486,159 A | 1/1996 | Mahurkar |
| 5,599,322 A | 2/1997 | Quinn |
| 5,607,405 A | 3/1997 | Decker et al. |
| 5,607,462 A | 3/1997 | Imran |
| 5,624,392 A | 4/1997 | Saab |
| 5,624,413 A | 4/1997 | Markel et al. |
| 5,665,067 A | 9/1997 | Linder et al. |
| 5,685,836 A | 11/1997 | DiPerna et al. |
| 5,738,649 A | 4/1998 | Macoviak |
| 5,776,111 A | 7/1998 | Tesio |
| 5,792,094 A | 8/1998 | Stevens et al. |
| 5,797,869 A | 8/1998 | Martin et al. |
| 5,807,318 A | 9/1998 | St. Goar et al. |
| 5,810,787 A | 9/1998 | Quinn |
| 5,810,789 A | 9/1998 | Powers et al. |
| 5,814,016 A | 9/1998 | Valley et al. |
| 5,830,196 A | 11/1998 | Hicks |
| 5,947,953 A | 9/1999 | Ash et al. |
| 5,961,486 A | 10/1999 | Twardowski et al. |
| 5,984,913 A | 11/1999 | Kritzinger et al. |
| 6,280,423 B1 | 8/2001 | Davey et al. |
| 6,409,700 B1 | 6/2002 | Siegel, Jr. et al. |
| 6,461,321 B1 * | 10/2002 | Quinn ................ 604/43 |
| 6,511,474 B1 | 1/2003 | Andersen |
| 6,517,529 B1 * | 2/2003 | Quinn ................ 604/528 |
| 6,540,714 B1 | 4/2003 | Quinn |
| 6,786,884 B1 * | 9/2004 | DeCant et al. ........ 604/43 |
| 6,808,501 B2 * | 10/2004 | Stess et al. ............ 602/6 |
| 7,108,674 B2 * | 9/2006 | Quinn ................ 604/43 |
| 7,419,479 B2 * | 9/2008 | Quinn ................ 604/270 |

FOREIGN PATENT DOCUMENTS

| | | |
|---|---|---|
| DE | 43 20 186 A1 | 12/1994 |
| EP | 0 495 263 A1 | 7/1992 |
| FR | 900.765 | 7/1945 |
| GB | 745379 | 2/1956 |
| WO | WO 97/17102 | 5/1997 |
| WO | WO 99/38550 * | 8/1999 |
| WO | WO 02/062407 A2 | 8/2002 |
| WO | WO 02/092159 A1 | 11/2002 |

* cited by examiner

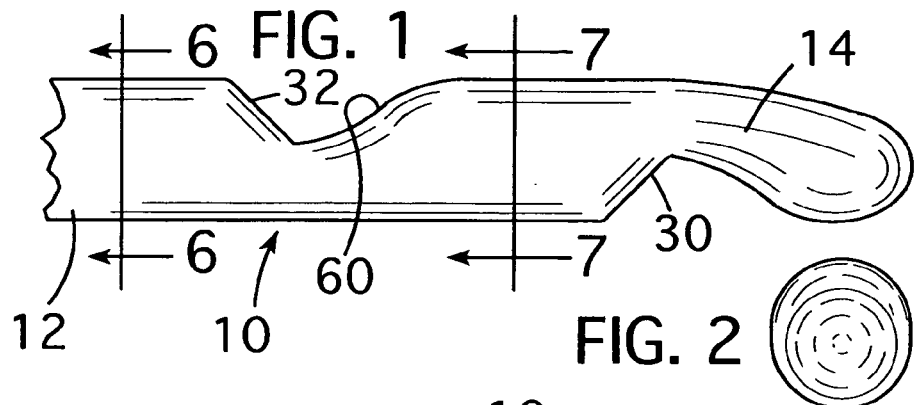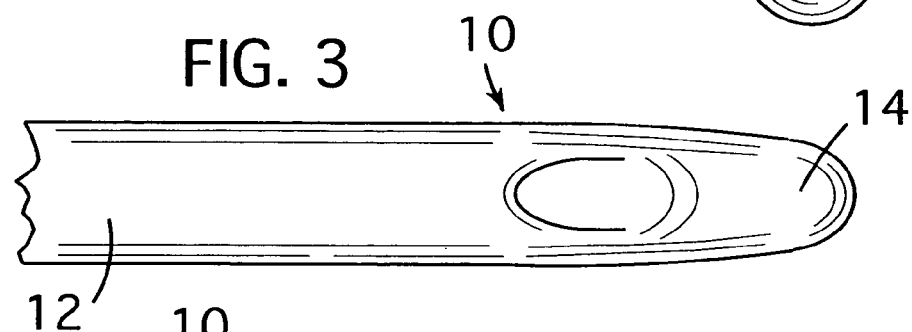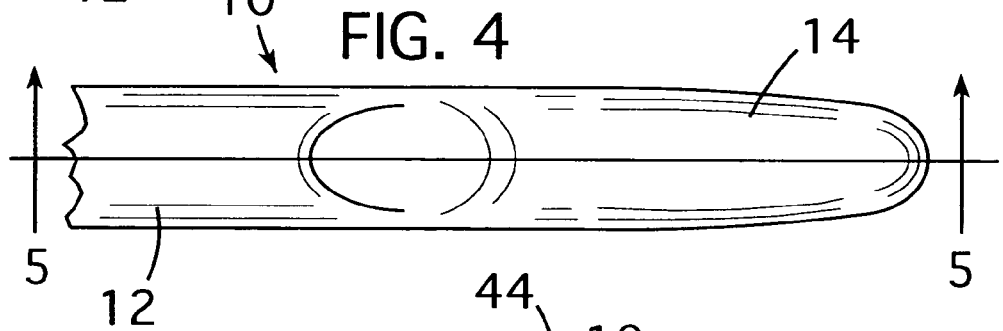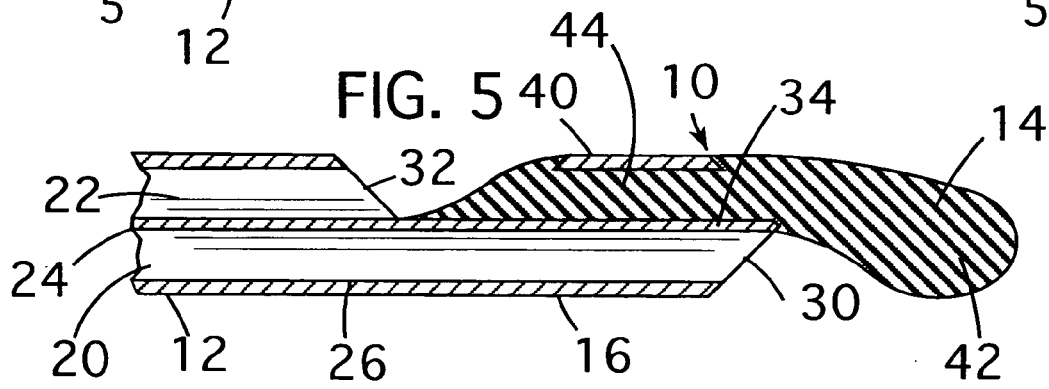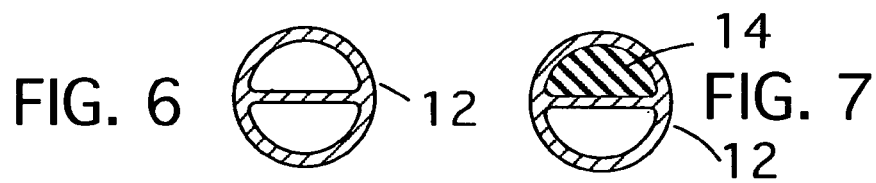

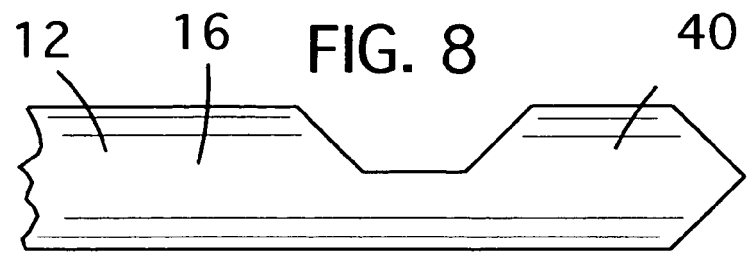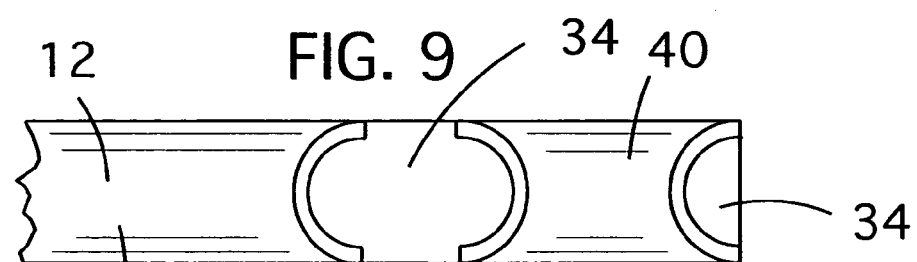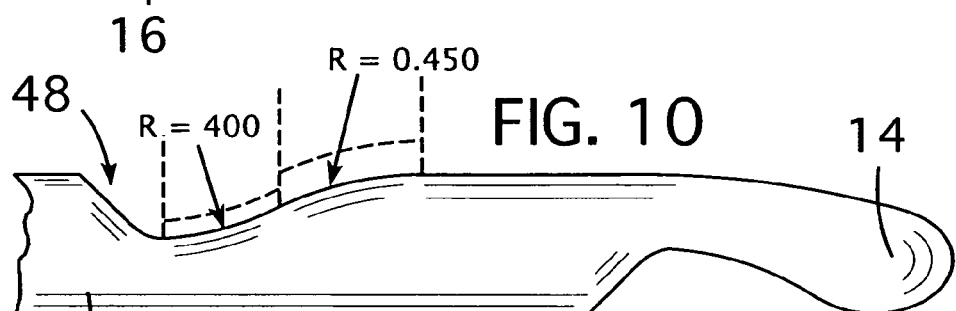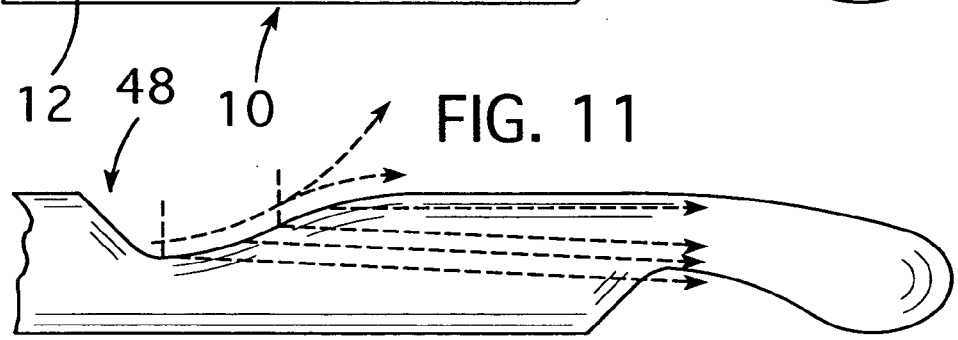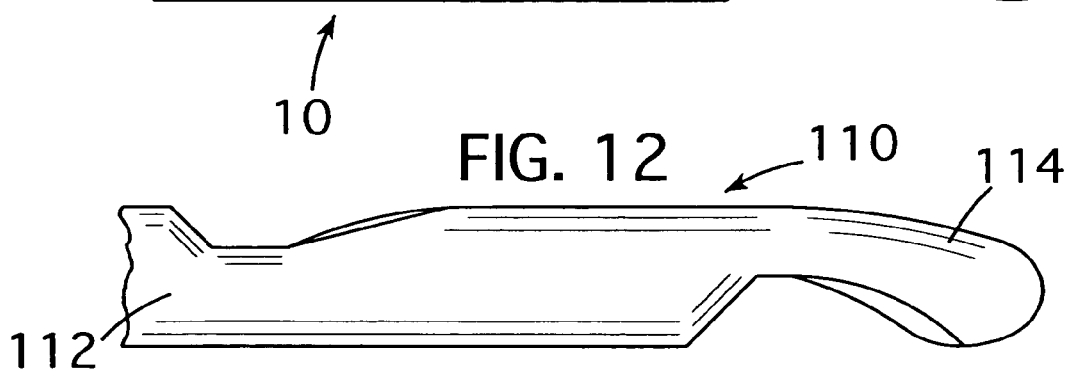

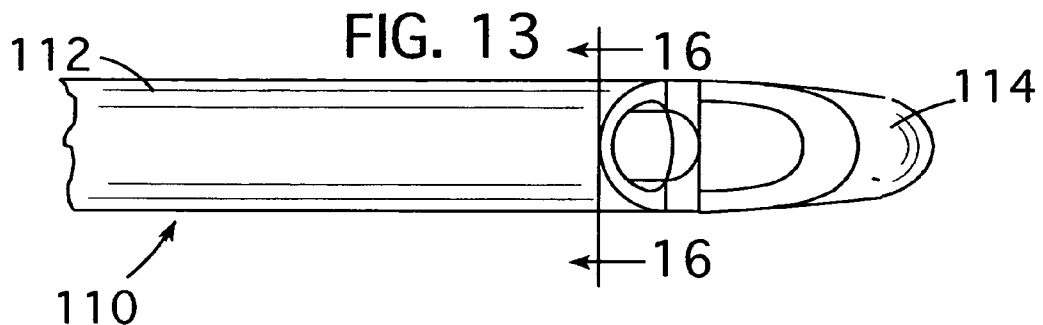
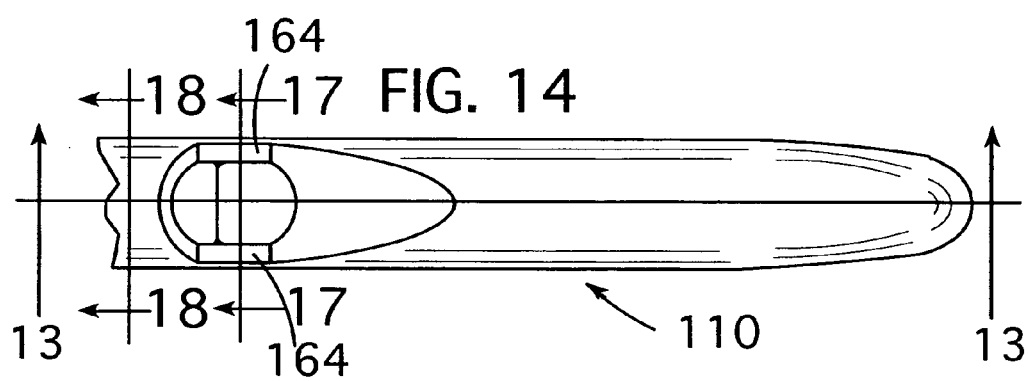
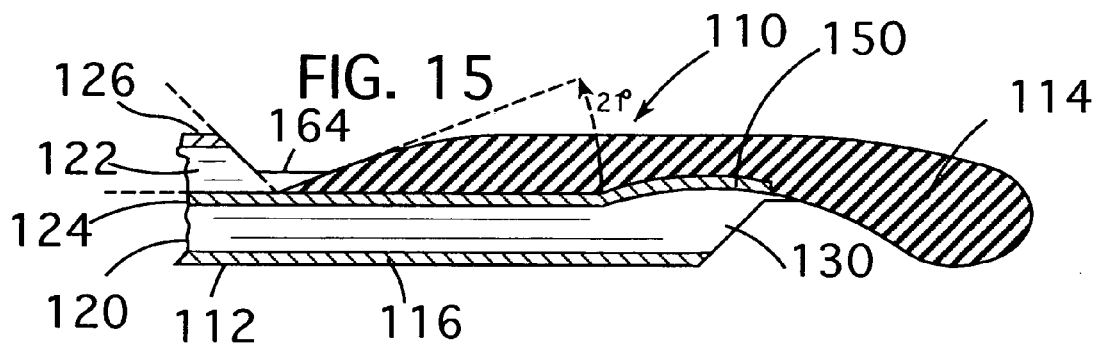
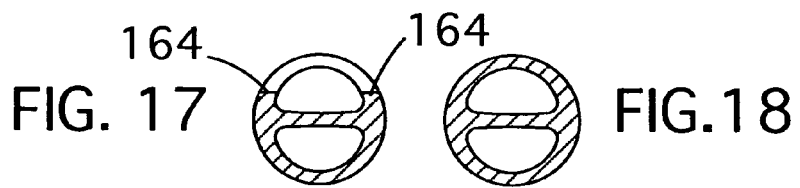

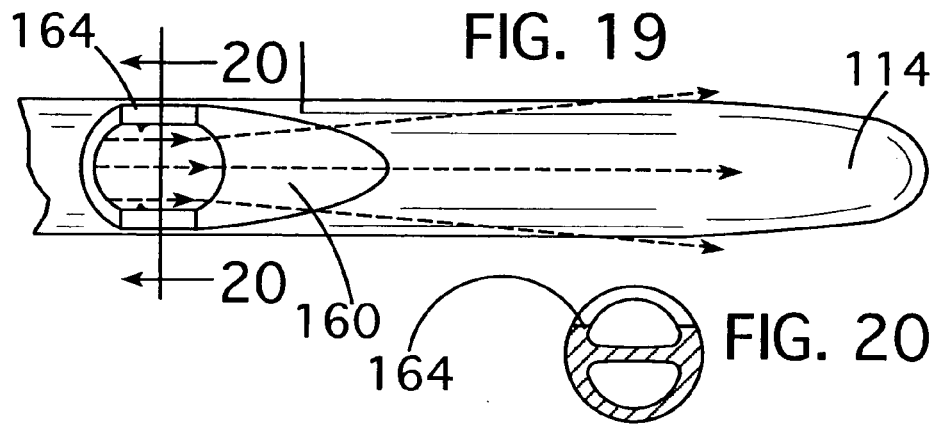
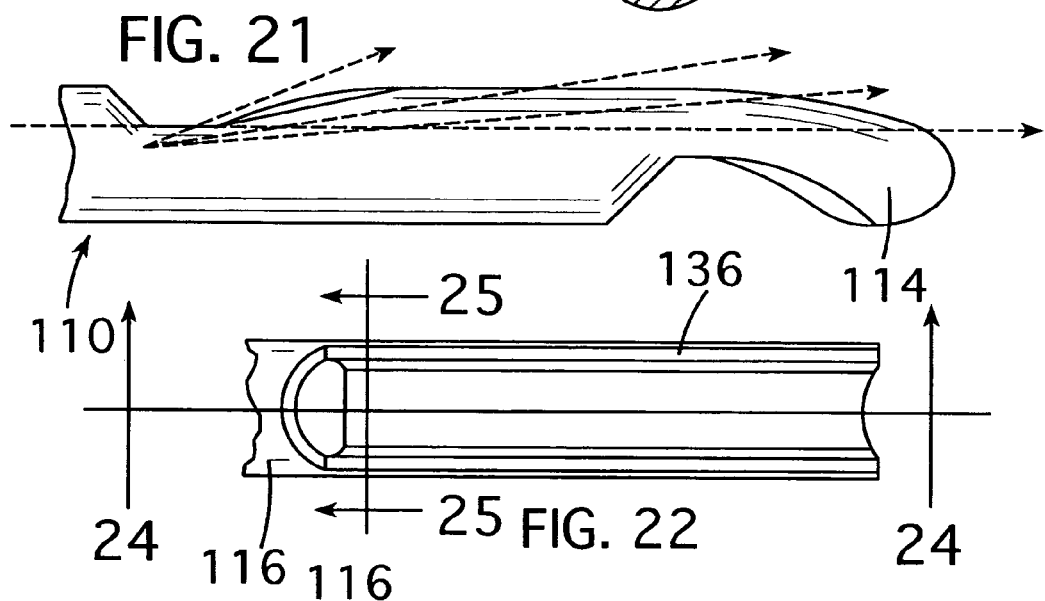
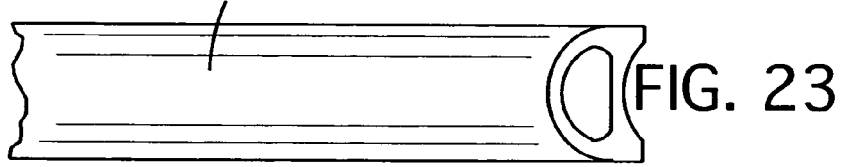
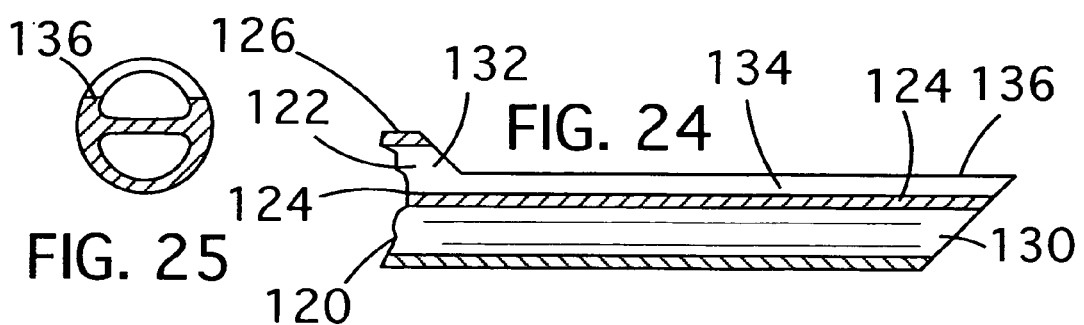

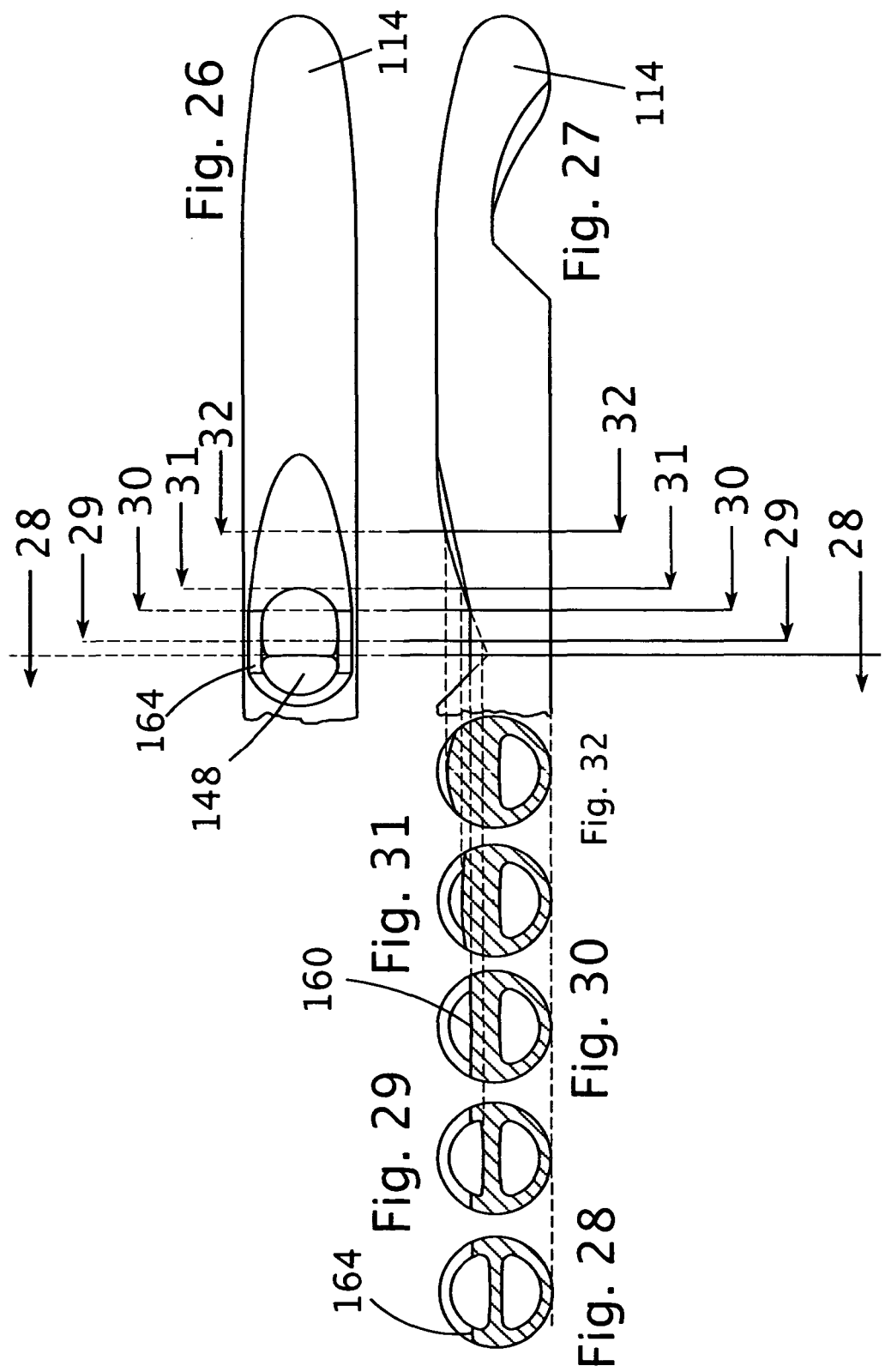

270

270

276  272

274

CATHETER AND METHOD OF MANUFACTURE

RELATED APPLICATION

This application is a continuation of International Application No. PCT US2004/037101 filed Nov. 5, 2004, which is related to Provisional U.S. Application Ser. No. 60/517,826, filed Nov. 6, 2003, and claims priority from that application.

FIELD OF THE INVENTION

The invention relates generally to catheters for use in intravenous applications. It relates particularly to hemodialysis catheters and methods of manufacturing them.

BACKGROUND OF THE INVENTION

Hemodialysis, as practiced today, normally employs one of two types of catheter to remove blood from the patient for processing and return processed blood to the patient. Most commonly, a catheter tube containing two lumens is used, each lumen having a generally semi-cylindrical or D-shape configuration. This type of catheter is frequently referred to as a dual lumen catheter. Alternatively, two tubes, each with a full cylindrical configuration, are used separately to remove blood for dialysis and return the processed blood.

Flow rates possible with conventional dual lumen catheters are usually lower than those achievable where separate tubes are used to remove blood from a vein for dialysis and then return processed blood back to the vein. Thus, the use of two tubes has become more and more popular as the capacity (maximum flow rate) of hemodialysis membranes has increased. However catheters utilizing two separate lumens are more difficult to insert and also take up considerably more space in the vessel, thereby somewhat compromising blood flow in the vessel.

Hemodialysis membranes are now able to process blood at over 500 ml of flow per minute. Even higher processing rates are foreseeable. However, problems occur with both the line introducing purified blood back into the vein (the venous or outflow line) and the line removing blood for purification (the arterial or intake line) at flow rates above 300 ml per minute. A high flow rate from the venous line may cause whipping or "fire-hosing" of the tip in the vein with consequent damage to the vein lining. A corresponding high flow rate into the arterial line may cause the port to be sucked into the vein wall, resulting in occlusion. It should be understood, of course, that both lines normally access the superior vena cava and the left atrium and the designations are used for differentiation purposes.

Speed of flow through a catheter lumen, whether it be in a single lumen or a dual lumen catheter, is controlled by a number of factors including the smoothness of the wall surface, the internal diameter or cross-sectional area of the tube lumen, and the length of the tube lumen. The most important factor is the cross-sectional area of the tube lumen. The force or speed of the fluid flow in a tube lumen for a given cross-sectional area is controlled by the external pumping force, of course. This is a positive pressure pushing processed blood through the venous lumen and a negative (suction) pressure pulling unprocessed blood through the arterial lumen.

Problems encountered in providing for a high flow rate through a catheter are magnified in a dual lumen catheter construction. Because each of the lumens in a dual lumen catheter normally has a D-shape, it has been assumed that flow rates are limited. Furthermore, such dual lumen catheters are, to a great extent, catheters with a main port that opens at the end of a lumen substantially on the axis of the lumen. Thus, "fire-hosing" frequently results. Fire-hosing may damage the vein wall, triggering the build-up of fibrin on the catheter tip. Fibrin build-up may result in port occlusion.

There are dual lumen catheters described in the prior art which utilize side ports for both outflow and inflow. An example is the catheter disclosed in the Cruz et al. U.S. Pat. No. 5,571,093. Another example is the catheter disclosed in Quinn U.S. Pat. No. 6,461,321. Yet another example is the catheter disclosed in the DeCant, Jr. et al. U.S. Pat. No. 6,786,884. Each of these catheter designs combines a dual lumen catheter tube with a dual passage bolus, which is independently formed and then attached to the distal end of the tube. Each has unique shortcomings in performance and/or manufacturability which detract from its attractiveness as a commercial product, however.

SUMMARY OF THE INVENTION

An object of the invention is to provide improved dual lumen hemodialysis catheters.

Another object is to provide dual lumen hemodialysis catheters which accommodate flow rates as high as the latest separate dual cylindrical lumen tubes and combined dual "D" lumen catheters.

Still another object is to provide dual lumen hemodialysis catheters which are capable of returning processed blood to the patient at high flow rates without harmful fire-hosing of the catheter tip.

Yet another object is to provide dual lumen hemodialysis catheters which permit high flow rates while minimizing trauma and potential red cell damage so as to substantially avoid clotting.

A further object is to provide dual lumen hemodialysis catheters in which occlusion of the return line port is substantially avoided regardless of the flow rate.

Another object is to provide dual lumen dialysis hemodialysis catheters in which occlusion of the return line port is substantially avoided regardless of the position of the port in relation to the vessel wall.

Still another object is to provide dual lumen hemodialysis catheters that facilitate reversal of the venous and arterial lines to relieve port occlusion without greatly increasing the potential for mixing of dialyzed blood with blood being removed for dialysis.

Yet another object is to provide a dual lumen catheter having an arterial port configuration that, in the reverse flow mode, directs the blood flow upward and forward along a 21° ramp angle immediately upon its point of exit from the lumen so as to direct the flow away from the venous port.

A further object is to provide an arterial port wherein, in the reverse flow mode, blood flows upward and forward along the 21° ramp angle immediately upon its point of exit from the lumen, which slows the flow and protects the blood components.

Yet a further object is to provide a dual lumen catheter that has rounded bullet tip portion that is smaller than the outside diameter of the tube so as to assist in insertion and minimize vessel wall damager.

Yet a further object is to provide a dual lumen hemodialysis catheter wherein a bolus tip is formed in place on a prepared distal end of a dual lumen catheter tube.

Yet a further object is to provide a dual lumen catheter that has rounded bullet tip portion that can be inserted using a tunneler and then placed in its final location without the utilization of a guide wire.

Still a further object is to provide a dual lumen catheter that has been rounded bullet tip portion that can be inserted using a tunneler and then placed in its final location over a guide wire, if desired.

The foregoing and other objects are realized in accordance with the present invention by providing dual lumen catheters comprising a catheter tube having first and second lumens of different length. The venous lumen half of the tube extends to a distal end well beyond the distal end of the arterial lumen half of the tube, leaving the septum between the lumens substantially exposed between those distal ends. A bolus tip which, in itself, contains no fluid passages, is insert molded onto that exposed septum.

The invention is embodied in two forms of hemodialysis catheter. In each the bolus tip includes a bullet nose section which extends forwardly of the distal end of the venous lumen and forms a flow direction ramp in front of the venous lumen opening, creating a venous port on one side of the catheter. The bolus tip also includes an attachment section which extends forwardly of the distal end of the arterial lumen and forms a flow direction ramp in front of the lumen opening, creating an arterial port on the opposite side of the catheter.

The foregoing and other objects are realized in accordance with the present invention by providing dual lumen catheters comprising a catheter tube having first and second lumens of different length. The venous lumen half of the tube extends to a distal end well beyond the distal end of the arterial lumen half of the tube, leaving the septum between the lumens substantially exposed between those distal ends. A bolus tip which, in itself, contains no fluid passages, is insert molded onto that exposed septum.

In one form of the invention, the venous port ramp begins at the point where the blood exits an ovoid lumen opening and travels over an ascending arc that slows and directs the flow forward, but also diffuses it, thereby softening the mixing of the infused blood with the normal venous flow. In this normal flow mode, blood is immediately carried forward and away from the aspirating arterial lumen, so some diffusion is desired. The ramp is fed by the ovoid shaped outlet end of the lumen that is formed in the manufacturing process from the original extruded "D" shape of the tube. This ovoid port is slightly larger than the "D", thereby slowing fluid flow. Its shape also raises the fluid outflow stream above the normal "D" septum, thereby assisting in the directional flow up and forward over the top of the bullet tip.

In this one form of the invention, the ramp in the arterial port differs from that in the venous port in several ways. Overall, the arterial port ramp is longer and, where it begins at the surface of the septum and the opening of the lumen, is slightly convex in cross-sectional shape. The ramp becomes flat as it continues radially outward and then slightly convex where it blends into the top surface. In the normal flow mode the longer ramp provides a larger recessed area to allow the maintenance of flow in the reversed flow mode. For this design a straight 21° angle ramp profile is highly preferred. The ramp angle may vary between 18° and 24° and still produce good results, however. Ramps with much larger profile angles, such as 45°, present an abrupt surface direction change and result in excessive diffusion around the sides of the tip that causes mixing in the reverse flow mode. Angles much smaller than 21°, such as 12° to 16°, do not provide enough upward flow direction and, also, result in unwanted mixing in the reversed flow mode.

In the normal aspiration mode, the rounded top distal end of the 21° angle ramp, in cooperation with the top of the inclined edge of the arterial lumen distal end, provide a protected area in the port which is created that assures the continuation of flow in the normal aspiration mode. Larger ramp angles reduce the size of the protected aspiration area. Smaller angles increase the length and size of the protected aspiration area but the additional length tends to allow the vessel wall to stretch and protrude into the protected area, thereby reducing its size and presenting the potential for port occlusion. The 21° angle presents the optimum ramp inclination for aspiration in normal flow, and in the reversed mode provides the maximum results for diffusion and flow direction.

Between the bullet nose section and the distal end opening of the arterial lumen, short side walls are formed on the exposed septum. These side walls serve two purposes. They control fluid flow and they stiffen the catheter at that point so that any tendency of the catheter to fold there is counteracted. The 45° angle of the proximal edge of the arterial port assures that there is no cross-sectional area reduction that would result in increased flow speed as the blood exits the port. Fluid can flow forward and upward without restriction. To further assure that there is no restriction to flow, the 21° angle ramp begins to rise from the floor of the port at the exact point where the leading edge of the 45° angle arterial lumen opening meets the beginning of the ramp, hence preventing any increased resistance to flow except by the ramp. The top edges of the side walls meet the 45° inclined edge of the arterial lumen opening behind the junction of the ramp and the surface of the lumen, after the ramp has ascended from the septum surface. The side walls contain the lower level of the fluid outflow that first meets the resistance of the ramp. As has been explained, the ramp tends to push flow upward (radially outward), but also tends to diffuse it around the tube. The side walls reduce the tendency for diffusion at this initial, and most critical point.

BRIEF DESCRIPTION OF THE DRAWINGS

The invention, including its construction and method of operation, is illustrated more or less diagrammatically in the drawings in which:

FIG. 1 is a side elevational view of a portion of a hemodialysis catheter embodying features of a first form of the invention;

FIG. 2 is a front end view of the catheter bolus of FIG. 1;

FIG. 3 is a bottom plan view of the bolus end of the catheter of FIG. 1;

FIG. 4 is a top plan view of the bolus for the catheter of FIG. 1;

FIG. 5 is a longitudinal sectional view taken through the bolus of the catheter of FIG. 4;

FIG. 6 is a cross-sectional view taken along line 6-6 of FIG. 1;

FIG. 7 is a cross-sectional view taken along line 7-7 of FIG. 1;

FIG. 8 is a side elevations view of the tube in the catheter of FIG. 1;

FIG. 9 is a top plan view of the tube seen in FIG. 1;

FIG. 10 is a side elevational view of the first form of catheter showing the compound curve slope of the ramp in front of the arterial lumen opening;

FIG. 11 is a side elevational view of the catheter of FIG. 10 illustrating fluid flow patterns;

FIG. 12 is a side elevational view of a portion of a hemodialysis catheter embodying features of a second form of the invention;

FIG. 13 is a bottom plan view of the catheter of FIG. 12

FIG. 14 is a top plan view of the catheter of FIG. 11

FIG. 15 is a longitudinal sectional view taken along line 15-15 of FIG. 14;

FIG. 16 is a cross-sectional view taken along line 16-16 of FIG. 11;

FIG. 17 is a cross-sectional view taken along line 17-17 of FIG. 14;

FIG. 18 is a cross-sectional view taken along line 16-16 of FIG. 14;

FIG. 19 is another top plan view of the catheter embodying features of the second form of the invention, showing the improved fluid flow patterns which are produced;

FIG. 20 is a cross-sectional view taken along line 20-20 of FIG. 19;

FIG. 21 is a side elevational view of the catheter and fluid flow patterns seen in FIG. 19;

FIG. 22 is a top plan view of the distal end of the catheter tube for the second form of catheter;

FIG. 23 is a bottom plan view to the tube portion seen in FIG. 22;

FIG. 24 is a longitudinal sectional view taken along line 24-24 of FIG. 22;

FIG. 25 is a cross-sectional view taken along line 25-25 of FIG. 22;

FIG. 26 is another top plan view of the second form of catheter;

FIG. 27 is another side elevational view of the second form of catheter;

FIG. 28 is a sectional view taken along line 28-28 of FIGS. 26 and 27;

FIG. 29 is a sectional view taken along line 29-29 of FIGS. 26 and 27;

FIG. 30 is a sectional view taken along line 30-30 of FIGS. 26 and 27;

FIG. 31 is a sectional view taken along line 31-31 of FIGS. 26 and 27;

FIG. 32 is a sectional view taken along line 32-32 of FIGS. 26 and 27;

DESCRIPTION OF THE PREFERRED EMBODIMENTS

Figure 33:
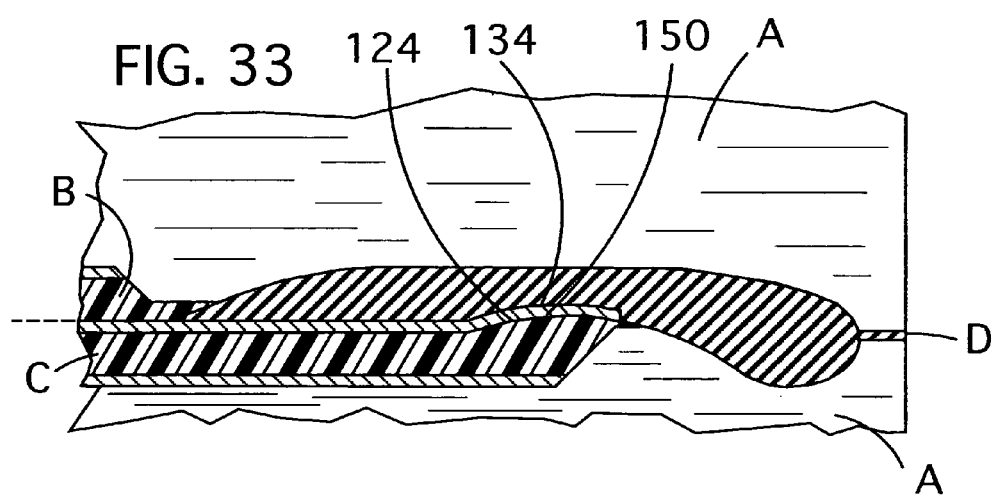
FIG. 33 is a longitudinal sectional view through a catheter embodying the second form of the invention as the bolus is insert molded onto the distal end of the tube.
Figure 34:
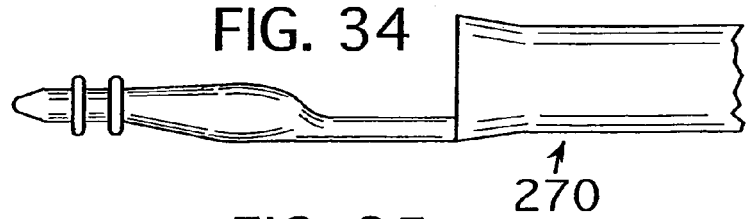
FIG. 34 is a side elevational view of a portion of a tunneling tool that is used to pull a catheter tip and catheter tube through a subcutaneous tunnel.
Figure 35:
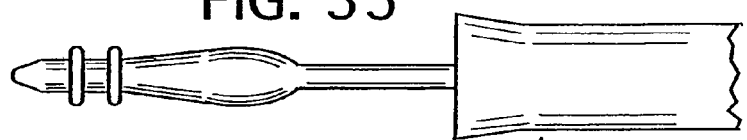
FIG. 35 is a top view of the tunneling tool.
Figure 36:
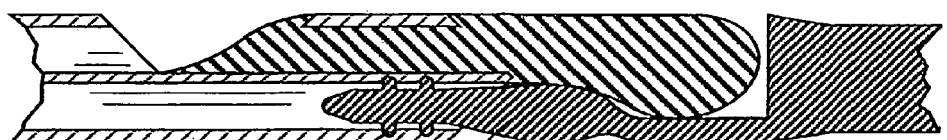
FIG. 36 is a longitudinal cross-sectional view of the tunneling tool after it is inserted into the venous lumen of a catheter tube.

Referring now to drawing FIGS. 1-11, a dual lumen catheter embodying features of a first form of the invention is shown generally at 10, with parts removed. The catheter 10 illustrated here is a dual-lumen hemodialysis catheter but it should be understood that the invention might find advantageous application in other intravenous treatment. The catheter 10 comprises a polyurethane catheter tube 12 onto which a polyurethane bolus tip 14 is insert molded.

The catheter tube 12 comprises a tube body 16 (see FIGS. 8 and 9) which contains a venous lumen 20 and an arterial lumen 22 separated by a septum 24. The lumens 20, 22 and the septum 24 are enclosed by a cylindrical body wall 26.

As best seen in FIG. 8, the venous lumen 20 has a distal end 30 which is cut off (skived) at a 45° angle to the septum 24 in the manner illustrated. The arterial lumen 22 has a distal end 32 which is displaced longitudinally from the end 30 of the venous lumen and is also cut off (skived) at a 45° angle to the septum 24. The upper surface 34 of the septum 24 is then, effectively, the outer surface of the tube 12 between the 45° angle skived ends 30 and 32.

In this first form of the catheter 10 invention, however, there is a short section 40 of the body wall 26 which remains between the lumen ends 30 and 32. As seen in FIG. 5, this wall section 40 overlies the bolus tip 14 after the tip is insert molded onto the tube 12, in a manner hereinafter discussed.

The bolus tip 14 is insert molded onto the tube 12 in a conventional manner. Referring to FIG. 5, the distal end of the tube 12 is placed in a suitably shaped die (not shown) with a gate where the end of the bullet nose on the bolus tip 14 is located. Molten plastic flows through the wall section 40 on the septum surface 34 and solidifies in the form illustrated. In doing so, it forms a bond with all complementary tube 12 surfaces.

The bolus tip 14 formed includes a bullet nose section 42 extending forwardly of the distal end 30 of the lumen 20. It also includes an attachment section 44 which is fastened to the lumen surface 34. The section 44 has a ramp 60 on its trailing face. The ramp 60 faces the open end 32 of the arterial lumen 22.

FIGS. 10 and 11 show the catheter 10 and the ramp 60 which, with the skived end 32 of the arterial lumen 22 forms the arterial port 48. FIG. 10 illustrates ramp angles and FIG. 11 illustrates fluid flow patterns.

Turning now to FIGS. 12-32, a portion of a dual lumen catheter embodying features of a second form of the invention is shown generally at 110. The catheter 110 comprises a catheter tube 112 onto which a bolus tip 114 is insert molded according to the invention.

The catheter tube 112 comprises a tube body 116 (see FIGS. 22-25) which contains a venous lumen 120 and an arterial lumen 122 separated by a septum 124. The lumens 120, 122 and the septum 124 are enclosed by a cylindrical body wall 126.

As best seen in FIG. 24, the venous lumen 120 also has a distal end 130 which is cut off (skived) at 45° to the septum 124, in the manner illustrated. The arterial lumen 122 has a distal end 132 which is displaced longitudinally from the end 130 of the venous lumen and is also cut off (skived) at 45° to the septum 124. One surface 134 of the septum 124 then forms the outer surface of the tube 112 between the 45° angle cut-off lumen ends 130 and 132. The tube 112 is formed with short side walls 136 which bracket the surface 134.

Referring now specifically to the FIG. 33, bolus tip 114 is insert molded onto the tube 112 in a conventional manner. Mold halves a form each side of the catheter. Before the mold is closed over tube 112, insert pin B is placed in arterial lumen 122. Insert pin C is inserted into the distal end of the venous lumen 120. The pin C has bulbous center section that stretches the septum 124 upwardly and outwardly adjacent its free end, at 150. Molten plastic is then introduced into the mold cavity through gate D.

The molten plastic adheres to the surface 134 of the septum 124 and to the side walls 136. Its temperature is effective to cause the bulge 150 formed in the thermoplastic septum 124 to retain this shape when the dies A and B and the pin C are removed.

The bolus tip includes a bullet nose section 142 extending forwardly of the distal end 130 of the lumen 120. It also includes an attachment section 144 which is fastened to the lumen surface 134 and the side walls 136.

Referring now specifically to FIGS. 26-32, the catheter 110 formed in this process has a ramp 160 facing the distal end 132 of the arterial lumen 122 and forming the arterial port 148. The ramp 160 is inclined at an angle of 21° to the septum 124. The ramp 160, where it meets the septum 124 at the base of cut-off lumen end 132, is slightly convex, as best seen in FIG. 29. The ramp 160 then becomes flat for a substantial (relative) distance, as best seen in FIG. 30. The ramp 160 then becomes increasingly concave, as best seen in FIGS. 31 and 32, to where it blends in with the tip surface. Adjacent the lumen end 132 the ramp 160 is bracketed by exposed portions 164 of the side walls 136.

Figure 37:
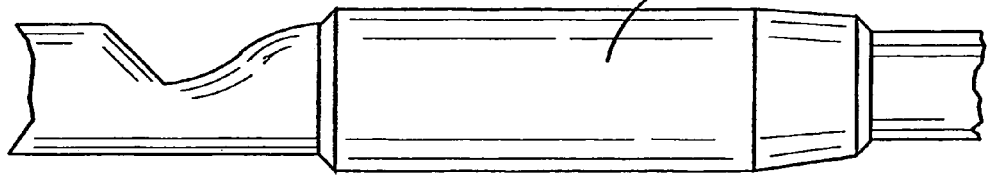
FIG. 37 is a side elevational view of a catheter tube and the tunneling tool secured together with an oversleeve and ready to be pulled through a tunnel.

FIGS. 34-37 illustrate a tunneller 270 and its use. The tunneller 270 works the same way as a conventional tunneller in that a connector probe 272 is forced into the venous lumen 122 of the tube 112. Then a retention sleeve 274 is placed over the tip 114 an tube 112 junction to help hold the parts together to make a smooth transition. The bulbous section 274, just behind the ribbed portion 276 that is inserted into the tube 114, is trapped behind the flexing tip 114 by the oversleeve 274 (FIG. 37). This makes separation of the parts virtually impossible.

Although both forms of the catheter invention which have been described provide substantial advantages over prior art dual lumen catheters, the second form is preferred. The side walls 136 in the arterial port reinforce the catheter at the port. Downward bending of the bolus tip is substantially prevented by the resistance of these side walls to stretching. Similarly, upward folding of the tip is substantially prevented by axial compression of the side walls.

Also, as previously discussed, the arterial ramp configuration provides substantial advantages. Initially, the slightly concave ramp channels flow (in the reverse flow mode) toward the center of the ramp. Subsequently, the 21° angle, flat ramp section continues to direct flow upwardly (radially outwardly). Finally the slightly convex ramp section encourages flow around the tip as it proceeds forwardly over the end of the tip. The result is that there is no substantial mixing flow, i.e., flow directly back toward the venous port.

While preferred embodiments of the invention have been described, it should be understood that the invention is not so limited, and modifications may be made without departing from the invention. The scope of the invention is defined by the appended claims, and all devices and methods that come within the meaning of the claims, either literally or by equivalence, are intended to be embraced therein.

The invention claimed is:

1. A blood vessel catheter assembly, comprising:
    a) an assembly of a polyurethane plastic catheter tube component and a polyurethane plastic bolus tip component;
    b) said catheter tube component containing a first lumen and a second lumen separated by a septum;
    c) said first lumen extending through said tube to an opening at a distal end of said first lumen and said tube;
    d) said second lumen extending through said tube to an opening at a distal end of said second lumen which is spaced from said distal end of said first lumen;
    e) said septum in said catheter tube having an exposed surface between said distal ends of said first and second lumens, and short side walls which bracket said exposed surface and extend separately from each other and substantially perpendicular to said septum;
    f) said bolus component including a leading nose section and a trailing attachment section;
    g) said attachment section being molded to said exposed surface of said septum and to each of said side walls;
    h) said nose section including an enlarged portion disposed in front of said first lumen opening in substantially axial alignment with said first lumen whereby a first port is formed in one side of said catheter between said first lumen opening and said enlarged portion and in communication with said first lumen;
    i) said attachment section including a ramp surface facing said opening in said distal end of said lumen;
    j) said ramp surface being inclined at an angle of between 18° and 24° away from said septum whereby a second port is formed in another side of said catheter between said second lumen opening and said ramp surface and in communication with said second lumen.

2. The catheter assembly of claim 1 further characterized in that:
    a) said enlarged portion of said bolus forms a substantially bullet shaped nose on the front end of said bolus.

3. The catheter assembly of claim 1 further characterized in that:
    a) said ramp surface has a trailing edge, said trailing edge being in substantial alignment with said opening in said second lumen where it meets said septum.

4. The catheter assembly of claim 1 further characterized in that:
    a) said ramp surface is flat along a portion of its length.

5. The catheter assembly of claim 1 further characterized in that:
    a) the angle of said ramp surface is about 21°.

6. The catheter assembly of claim 1 further characterized in that:
    a) said opening at the distal end of said second lumen has an edge which is inclined at an angle of about 45° to said septum.

7. The catheter assembly of claim 1 further characterized in that:
    a) said ramp surface is also convex in cross-section along a portion of its length.

8. The catheter assembly of claim 7 further characterized in that:
    a) said ramp surface is also concave in cross-section along a portion of its length.

9. The catheter assembly of claim 8 further characterized in that:
    a) said ramp is flat between said concave and convex portions.

10. The catheter assembly of claim 1 further characterized in that:
    a) said enlarged portion of said nose section has a smaller circumference than the outside of said catheter tube adjacent where said first port is formed.

11. The catheter assembly of claim 10 further characterized in that:
    a) said nose section is inclined at an angle to the septum surface in the radial direction of said first lumen.

12. The catheter assembly of claim 1 further characterized in that:
    a) said catheter tube and said bolus are both formed of thermoplastic material;
    b) said bolus being formed in place on said catheter tube.

13. A blood vessel catheter assembly, comprising:
    a) a plastic catheter tube component and a plastic bolus tip component formed independently from said tube component and fastened to said tube component;
    b) said catheter tube component containing a first lumen and a second lumen separated by a septum;

c) said first lumen extending through said tube to an opening at a distal end of said first lumen and said tube;
d) said second lumen extending through said tube to an opening at a distal end of said second lumen which is spaced from said distal end of said first lumen;
e) said septum in said catheter tube having an exposed surface between said distal ends of said first and second lumens, and said catheter tube including two short side walls which bracket said exposed surface of said septum and extend substantially upright from said septum;
f) said bolus component including a leading nose section and a trailing attachment section;
g) said attachment section being molded to said exposed surface of said septum and to said side walls so as to bond said attachment section of said tip component to said septum and side walls of said tube component;
h) said nose section including an enlarged portion disposed in front of said first lumen opening in substantially axial alignment with said first lumen whereby a first port is formed in one side of said catheter between said first lumen opening and said enlarged portion and in communication with said first lumen;
i) said attachment section including a ramp surface facing said opening in said distal end of said lumen;
j) said ramp surface being inclined at an angle of between 18° and 24° away from said septum whereby a second port is formed in another side of said catheter between said second lumen opening and said ramp surface and in communication with said second lumen.

* * * * *